United States Patent
Tiedje

(10) Patent No.: US 9,010,327 B2
(45) Date of Patent: Apr. 21, 2015

(54) ENERGY RELIEF CONTROL IN A MECHANICAL VENTILATOR

(75) Inventor: Mikael Tiedje, Hisings-Kärra (SE)

(73) Assignee: Breas Medical AB, Molnlycke (SE)

( * ) Notice: Subject to any disclaimer, the term of this patent is extended or adjusted under 35 U.S.C. 154(b) by 822 days.

(21) Appl. No.: 12/306,366

(22) PCT Filed: Jul. 2, 2007

(86) PCT No.: PCT/SE2007/000650
§ 371 (c)(1),
(2), (4) Date: Dec. 23, 2008

(87) PCT Pub. No.: WO2008/002252
PCT Pub. Date: Jan. 3, 2008

(65) Prior Publication Data
US 2009/0188502 A1    Jul. 30, 2009

Related U.S. Application Data

(60) Provisional application No. 60/806,371, filed on Jun. 30, 2006.

(51) Int. Cl.
*A61M 16/00* (2006.01)
*A62B 7/00* (2006.01)
(Continued)

(52) U.S. Cl.
CPC .......... *A61M 16/0051* (2013.01); *A61M 16/06* (2013.01); *A61M 2016/0021* (2013.01); *A61M 2016/0027* (2013.01); *A61M 2016/003* (2013.01); *A61M 2205/3553* (2013.01); *A61M 2205/3569* (2013.01); *A61M 2205/3584* (2013.01); *A61M 2205/3592* (2013.01); *A61M 2205/502* (2013.01); *A61M 2205/52* (2013.01); *A61M 2230/04* (2013.01); *A61M 2230/10* (2013.01); *A61M 2230/18* (2013.01); *A61M 2230/205* (2013.01); *A61M 2230/30* (2013.01); *A61M 2230/432* (2013.01); *A61M 2230/435* (2013.01); *A61M 2230/50* (2013.01); *A61M 16/0069* (2013.01); *A61M 16/0627* (2013.01)

(58) Field of Classification Search
USPC ............. 128/204.23, 204.18, 204.21, 204.22, 128/204.26, 204.29, 205.22, 205.23, 128/207.14–207.17; 600/529–533, 600/537–539
See application file for complete search history.

(56) References Cited

U.S. PATENT DOCUMENTS 5,161,525 A * 11/1992 Kimm et al. ............. 128/204.26
5,245,995 A * 9/1993 Sullivan et al. .......... 128/204.23
(Continued)

FOREIGN PATENT DOCUMENTS

WO    WO 2006/047826  A1    5/2006

OTHER PUBLICATIONS

Extended European Search Report mailed Jul. 3, 2014 for European Application No. 07748309.7.

*Primary Examiner* — Tan-Uyen (Jackie) T Ho
*Assistant Examiner* — Mark K Han
(74) *Attorney, Agent, or Firm* — Alan Taboada; Moser Taboada

(57) ABSTRACT

The present invention relates to a solution for controlling the pressure/flow of breathing gas to a mechanical ventilator (4) by using an energy of breathing analysis and further to provide a pressure relief during exhalation and a trigger determination when to start the pressure relief using energy content of breathing in analysis for determining a pressure curve form during at least a portion of the expiration phase.

17 Claims, 3 Drawing Sheets

(51) Int. Cl.
*F16K 31/02* (2006.01)
*A61M 16/06* (2006.01)

(56) References Cited

U.S. PATENT DOCUMENTS

| | | | |
|---|---|---|---|
| 5,259,373 A * | 11/1993 | Gruenke et al. | 128/204.23 |
| 5,443,061 A | 8/1995 | Champain et al. | |
| 5,551,419 A * | 9/1996 | Froehlich et al. | 128/204.23 |
| 5,740,795 A * | 4/1998 | Brydon | 128/204.21 |
| 6,484,719 B1 * | 11/2002 | Berthon-Jones | 128/204.23 |
| 6,820,618 B2 * | 11/2004 | Banner et al. | 128/204.23 |
| 6,910,481 B2 * | 6/2005 | Kimmel et al. | 128/204.23 |
| 6,932,084 B2 * | 8/2005 | Estes et al. | 128/204.18 |
| 6,968,842 B1 * | 11/2005 | Truschel et al. | 128/204.18 |
| 2005/0005936 A1 * | 1/2005 | Wondka | 128/204.18 |
| 2005/0034721 A1 * | 2/2005 | Freitag | 128/200.24 |
| 2005/0247315 A1 * | 11/2005 | Estes et al. | 128/204.23 |
| 2006/0021618 A1 * | 2/2006 | Berthon-Jones et al. | 128/204.18 |
| 2006/0196508 A1 | 9/2006 | Chalvignac | |
| 2008/0283061 A1 | 11/2008 | Tiedje | |

* cited by examiner

ENERGY RELIEF CONTROL IN A MECHANICAL VENTILATOR

TECHNICAL FIELD

The present invention relates to a mechanical ventilator and in particular for a solution for providing a comfortable breathing for users of the ventilator.

BACKGROUND OF THE INVENTION

Patients suffering from different forms of breathing disorders can be subject to several types of treatments depending on the illness or disorder present. Such treatments include surgical procedures, pharmacologic therapy, and non-invasive mechanical techniques. Surgical techniques to remedy breathing disorders constitute a considerable risk for the patient and can lead to permanent injury or even mortality. Pharmacologic therapy has in general proved disappointing with respect to treating certain breathing disorders, e.g. sleep apnea. It is therefore of interest to find other treatments, preferably non-invasive techniques.

A mechanical ventilator represents a non-invasive technique for treatment of certain breathing disorders such as ventilatory failure, hypoventilation, and periodic breathing during sleep and awake and in sleep apnea that occurs exclusively during sleep. Ventilatory failure includes all forms of insufficient ventilation with respect to metabolic need whether occurring during wake or periods of sleep. Hypoventilation and periodic breathing, in its most frequently occurring form referred to as Cheyne-Stokes ventilation, may occur periodically or constantly during wake or sleep. Conditions associated with hypoventilation, in particular nocturnal hypoventilation include e.g. central nervous system disorders such as stroke, muscular dystrophies, certain congenital conditions, advanced chronic obstructive pulmonary disease (COPD), etc. Cheyne-Stokes ventilation or various forms of central apnea are commonly associated with cardiac and circulatory disorders, in particular cardiac failure.

Ventilatory failure is a potentially life threatening condition. The general comorbidity in patients with failing ventilation is considerable. The condition is highly disabling in terms of reduced physical capacity, cognitive dysfunction in severe cases and poor quality of life. Patients with ventilatory failure therefore experience significant daytime symptoms but in addition, the majority of these cases experience a general worsening of their condition during state changes such as sleep. The phenomenon of disordered breathing during sleep, whether occurring as a consequence of ventilatory failure or as a component of sleep apnea in accordance with the description above causes sleep fragmentation. Daytime complications include sleepiness and cognitive dysfunction. Severe sleep disordered breathing occurring in other comorbid conditions like obesity, neuromuscular disease, post polio myelitis states, scoliosis or heart failure may be associated with considerable worsening of hypoventilation and compromised blood gas balance. Sleep apnea has been associated with cardiovascular complications including coronary heart disease, myocardial infarction, stroke, arterial hypertension, thrombosis, and cardiac arrhythmia. It is therefore of both immediate and long-term interest to reduce the exposure to sleep disordered breathing.

Recent advancement in mechanical non-invasive ventilator techniques includes administration of continuous positive airway pressure (CPAP) in different forms of sleep disordered breathing. During CPAP administration an elevated airway pressure is maintained throughout the breathing phase during a period coinciding with sleep. In sleep apnea this procedure may provide appropriate stabilization of the upper airway thereby preventing collapse. This, so called mono-level CPAP therapy, provides an almost identical pressure during inhalation and exhalation. Not only may CPAP be uncomfortable for the patient due to a sensed increased work of breathing during ventilation, specifically expiration. Some forms of apnea, mainly including those of central origin, and most forms of hypoventilation are only poorly controlled by CPAP. A more recently developed bi-level CPAP system administers different pressure levels during inhalation and exhalation. Bi-level CPAP provides increased comfort for most patients and not infrequently, an improved clinical response. Bi-level CPAP provides two pressure levels, Inspiratory Positive Airway Pressure (IPAP) and Expiratory Positive Airway Pressure (EPAP). IPAP is administered during the inhalation phase while EPAP is given during the exhalation phase.

In CPAP treatment it is crucial that the CPAP system complies with the patient's inspiratory and expiratory effort to make the treatment comfortable. A system that does not comply with patient efforts creates an air trapping situation and increase discomfort for the patient as well as considerably increasing the possibility of anxiety for the patient. One key component in such systems is the ability to sense the patient rhythm or breathing phases.

Especially for patients new to treatment using mechanical ventilators there is a difficulty in accepting the treatment and they often do not use their equipment throughout treatment sessions, such as for instance the entire night if they are under treatment of obstructive sleep apnea (OSA). This can often be the case if they feel that it is difficult to exhale against the positive pressure that is provided by the ventilator.

The object of the invention is to overcome some of the deficiencies associated with known technology.

SUMMARY OF THE INVENTION

This is achieved by providing a ventilator that reduces the positive pressure dynamically during the expiration period of the breathing cycle. By measuring the patient's inspiratory effort and use the effort value during expiratory phase it is possible to increase the patient's comfort, reduce air trapping, and possibly reduce anxiety.

The invention is realized in a number of aspects wherein a first aspect is provided, a mechanical ventilator for treatment of breathing disorders, comprising a controllable pressure and breathing gas flow generator wherein the ventilator is arranged to determine the energy of breathing using current and voltage supplied to the generator. Furthermore, input parameters may be used for determining a trigger point between an inspiration and expiration phase of a breathing cycle and wherein the ventilator is controllable to reduce the pressure during a period of time during the expiration phase of the breathing cycle; the amount of pressure reduction is determined from an energy of breathing analysis.

The energy of breathing may be determined by measuring the current and voltage supplied to the motor driving pressure and flow generator or the energy of breathing may be determined by measuring the pressure and flow supplied to the patient.

Another aspect of the present invention, a method of increasing the comfort for a patient using a mechanical ventilator is provided, comprising the steps of:

measuring a plurality of parameters during a inspiration phase of a breathing cycle;

determining a trigger point between the inspiration phase and a subsequent expiration phase;

determining a curve form of a pressure signal using an energy of breathing analysis;

controlling the pressure of the breathing air from the ventilator using the determined curve form signal during at least a portion of the expiration phase.

Yet another aspect of the present invention, a mechanical ventilator system is provided, comprising a mechanical ventilator as described above, a breathing mask, a breathing air conduit between the mechanical ventilator and mask, and sensors for measuring data indicative of breathing condition and mechanical ventilator condition for use in a controller for controlling the supply of pressure and/or flow of breathing gas from the mechanical ventilator.

BRIEF DESCRIPTION OF THE DRAWINGS

In the following the invention will be described in a non-limiting way and in more detail with reference to exemplary embodiments illustrated in the enclosed drawings, in which.

DETAILED DESCRIPTION OF PREFERRED EMBODIMENTS

Figure 1:
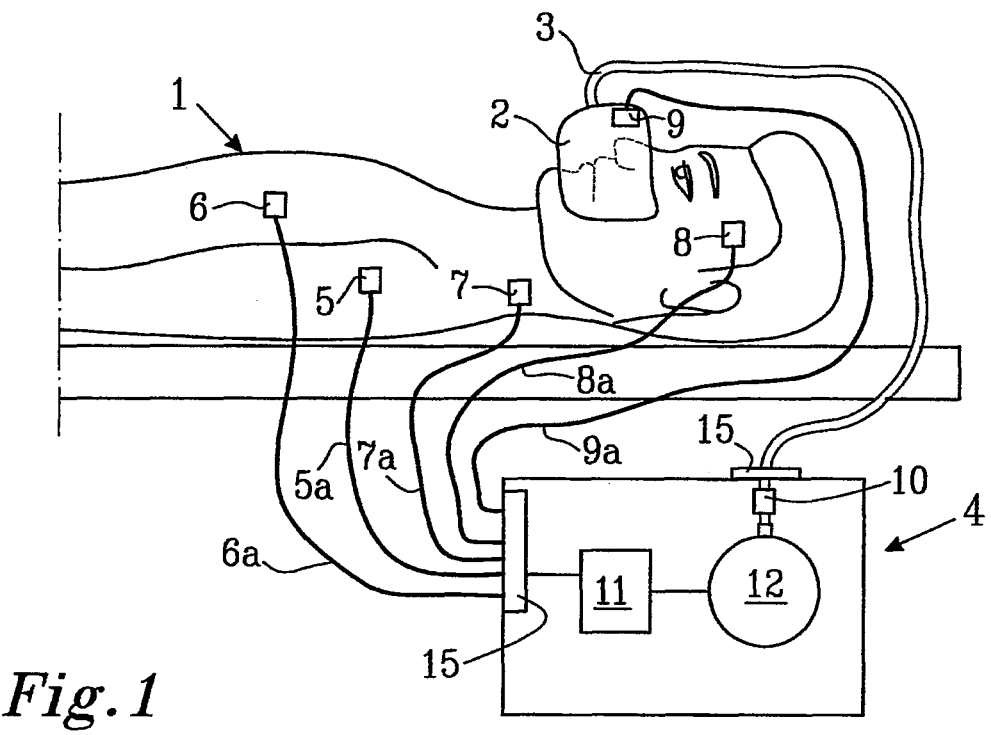
FIG. 1 illustrates schematic of a breathing circuit system according to the present invention.

In FIG. 1 a schematic mechanical ventilation system used for the treatment of hypoventilation disorders is depicted. A ventilation system comprise a mechanical ventilator 4 supplying pressurized breathing gas, tubing 3 for guiding breathing gas to the patient 1, a breathing mask 2 or similar for administrating the breathing gas to the patient 1, sensing means 5, 6, 7, 8, 9 and 10 for determining the physiological status of the patient 1. The number of sensors connected to the mechanical ventilator may be one or more; however, in a preferred embodiment of the present invention at least one sensor is necessary: a breathing gas flow measurement which may be located essentially anywhere along the breathing gas tubing or in the mask. A mechanical ventilator 4 is supplying breathing gas for instance as a positive airway pressure via a tubing 3 and through a mask 2 to a patient 1. The mask 2 can be a face mask 2 covering both the mouth and nose or a nasal mask covering only the nose or nostrils depending on the patients needs. It can also be a hood covering the complete head or body of the patient. The ventilator may be used for administering a number of different treatment methods including but not limited to CPAP (Continuous Positive Airway Pressure), Auto CPAP (e.g. using a neural network), PAV (Proportional Assist Ventilation), PEEP (Positive End-Expiratory Pressure), and PSV (Pressure Support Ventilation).

The breathing gas may be of any suitable gas composition for breathing purposes as understood by the person skilled in the art, the composition may depend on the physiological status of the patient and the treatment of interest.

The pressure or flow from the ventilator 4 is controlled by a processing unit 11 as shown in FIG. 1. The processing unit 11 may involve a computer program that receives one or several input parameters 5, 6, 7, 8, 9, and 10 obtained from the patient 1 describing the physiological status of the patient and pressure/flow data indicative of breathing gas system configuration and status. Data indicative of patient status is obtained using sensors 5, 6, 7, 8, 9, and 10 connected to the patient and transferred to the processing unit 11 via connection means 5a, 6a, 7a, 8a, and 9a (connection means for sensor 10 is not depicted in FIG. 1 since the sensor may be placed at several different locations, such as inside the ventilator apparatus) and an interface (15) in the ventilator (4). These input parameters may be for instance flow or pressure signals, data obtained from EEG, EMG, EOG, and ECG measurements, O2 and/or CO2 measurements in relation to the patient, body temperature, blood pressure, SpO2 (oxygen saturation), eye movements, and sound measurements. It should be understood that the invention is not limited to the above mentioned input parameters but other input parameters may be used. In FIG. 1 not all sensors 5, 6, 7, 8, 9, and 10 and sensor connection means 5a, 6a, 7a, 8a, and 9a are depicted, only a subset is shown in order to illustrate a schematically view of the system and the depicted locations are only given as examples and are in no way limiting to the invention, e.g. the flow signal may be measured at either the mask location or close to the mechanical ventilator or at both locations in order to deduce a differential signal if this is required.

The flow sensor 10 may be located at several different positions, e.g. in the breathing air tubing 3 at any suitable position, such as close to the mechanical ventilator apparatus (or even within the ventilator housing) or in the vicinity of the mask.

The input data is then supplied to a processing device 11 via the interface (15).

Figure 2:
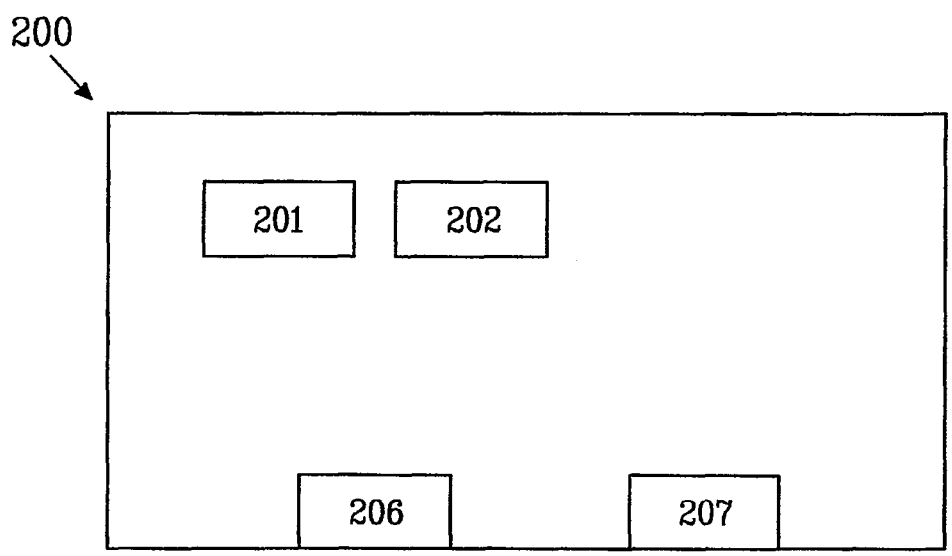
FIG. 2 is a schematic block diagram of a ventilator apparatus according to the present invention.

In FIG. 2, the processing device 200 comprises at least computational unit 201, where the computational or processing unit 201 analyses the measured data, e.g. data from flow and pressure measurements, according to an appropriate method, algorithm or algorithms (to be discussed in detail below) in order to determine an appropriate response and send control signal or signals to a mechanical ventilator unit 12. This mechanical ventilator unit 12 may be a fan 12 arranged to deliver appropriate amounts of breathing gas at specified and controlled pressure levels. The processing device 200 may be located within the ventilator 4 or in an external device used for controlling the ventilator and/or analysing data for and from the ventilator.

The processing device 200 may also comprise a data storage unit 202 for post analysis and inspection and also a connection for an internal or external non-volatile memory device, like for instance a memory device using a USB connection, an external hard drive, a floppy disk, a CD-ROM writer, a DVD writer, a Memory stick, a Compact Flash memory, a Secure Digital memory, an xD-Picture memory card, or a Smart Media memory card. These are only given as examples, and are not limiting for the invention, many more non-volatile memory devices may be used in the invention as appreciated by the person skilled in the art. The processing unit may have an input for receiving data indicative of the voltage and current supplied to the motor driving the mechanical ventilator (e.g. a fan).

The mechanical ventilator 12 may also have input means (not shown) for manually setting control parameters and other parameters necessary for the operation of the device.

Through a first and a second communication means 206 and 207 illustrated in FIG. 2 it is possible to communicate with the device 4 to and from an external computational device or one of the flow sensors (5, 6, 7, 8, 9, 10) for retrieving data and results for immediate and/or later analysis and/or inspection. The communication means can be of a serial type like for instance according to the standards RS232, RS485, USB, Ethernet, or Fire wire, or of a parallel type like for instance according to the standards Centronics, ISA, PCI, or GPIB/HPIB (General purpose interface bus). It may also be any wireless system of the standards in the IEEE 802.11, 802.15, and 802.16 series, HiperLAN, Bluetooth, IR, GSM, GPRS, or UMTS, or any other appropriate fixed or wireless communication system capable of transmitting measurement data. It can also be of any proprietary non-standardized communication formats, whether it is wireless or wired.

The ventilator device 4 may also have display means (not shown) for displaying measured data and obtained response parameters for use by a physician, other medical personnel, or the patient. The display means may be of any normal type as appreciated by a person skilled in the art. The data is displayed with such a high rate that a real time feedback is provided to a person monitoring the ventilator characteristics and function for immediate feedback and control.

The processing device 200 can use different input parameters for calculating the energy of breathing. For instance using the current and voltage supplied to the motor of the fan can be used for determining the energy input into the ventilator system and thus related to the energy of breathing. Another way of determining the energy of breathing is to measure the flow and pressure and use these two parameters in a calculation for determining the energy of breathing.

Breathing Energy Equation $$m\left(\frac{P_1}{\rho} + \frac{V_1^2}{2} + g*z_1\right) + W_{fan} = m\left(\frac{P_2}{\rho} + \frac{V_2^2}{2} + g*z_2\right) + W_{patient} + E_{friction}.$$  Eq. 1

The amount and weight of gas inspired by patient and amount of gas expired by patient is in a balanced system equal though the pressure and flow can vary during inspiration and expiration. Since the total energy exchanged over a complete breathing cycle between CPAP system and patient is constant Eq.1 may be transposed to:

$$W_{fan} = +W_{patient} + E_{friction}$$  Eq.2.

Measuring the fan motor current and voltage during inspiration is then a reflection of the energy given during the inspiratory phase. The energy data collection is done at a rate of 20 Hz; however, it should be noted that other data rates may be applicable, e.g. within the range of 1-1000 Hz, and in more particular in the range of 5-100 Hz. Other sampling rates are also possible (1000 Hz and higher) but may not necessarily contribute to the understanding of the system unless over sampling is used for filtering and/or statistical purposes.

The inspiration accumulated energy is summed together as below:

Exhalation Energy Reduction Calculation $$E_{inh} = \sum_{n=0}^{n=n_{exh}} \Delta E_n.$$  Eq 3

The inhalation energy calculated is used to calculate the energy reduction for the exhalation period. The Energy Relief factor: ($ER_{factor}$) shall be used to adjust the exhalation pressure ($P_{er}$).

$$P_{er} = \frac{(E_{inh} * ER_{factor})}{E_{exh}}.$$  Eq 4

The $ER_{factor}$ may be settable from a user interface, settable through an administration interface, factory determined, or coupled to some breathing related sensor input.

Using the determined energy of breathing it is possible to determine a pressure relief to be used during an expiration period when the inspiration period is over. The system according to the present invention is arranged to reduce the positive pressure during expiration period and such a reduced pressure during expiration period are for many users experienced as more comfortable. The reduction of pressure during the expiration period can vary but should come back to the base pressure at the end of the expiration period when the inspiration period starts.

Figure 3:
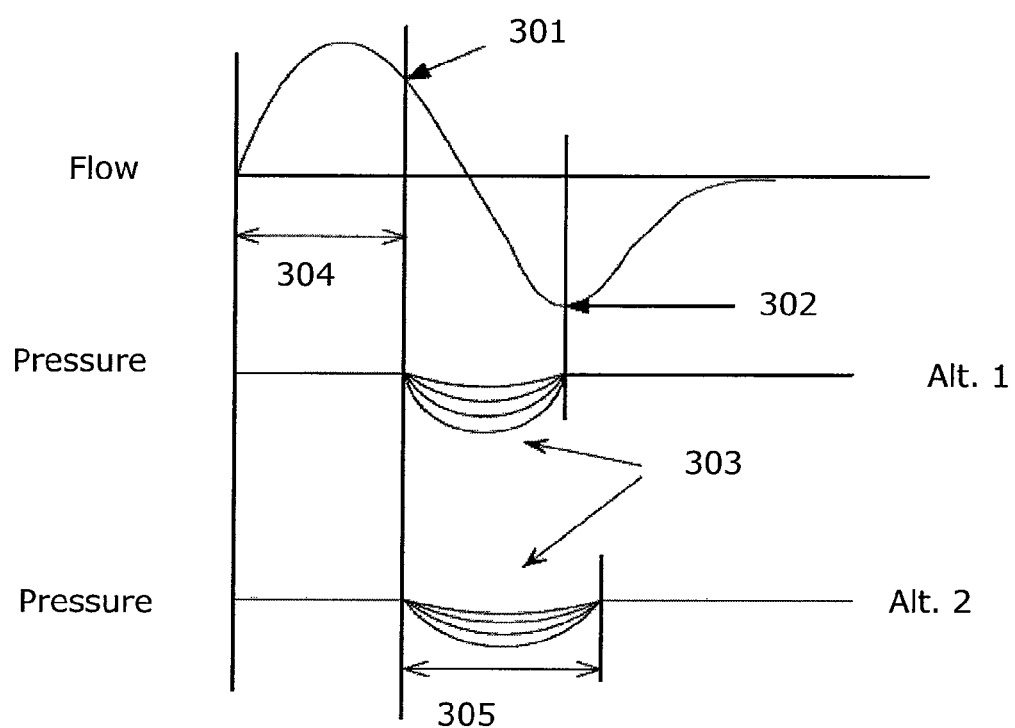
FIG. 3 illustrates a schematic breathing cycle.

Examples of pressure and flow versus time during inspiration and expiration periods are shown in FIG. 3. It can be seen in the figure that different curve forms can be applied during the expiration period. In FIG. 3 two different alternatives (Alt. 1 and Alt. 2) are shown. The upper curve shows the flow with an expiration trigger point 301 marked and an exhalation max flow point 302 marked. The inspiration time is indicated 304. The two alternatives show two different ways of applying pressure exhalation pressure relief periods 303.

The system may determine the triggering point 301 between the inspiration and expiration phases by a number of different methods, for instance using energy of breathing based analysis.

Figure 4:
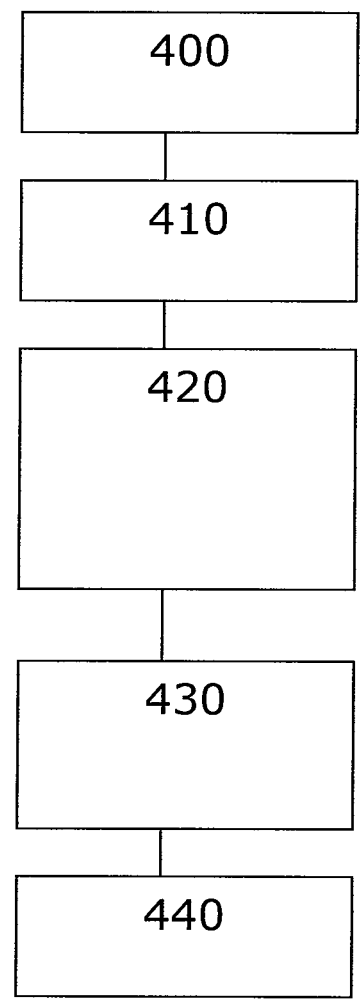
FIG. 4 illustrates a method according to the present invention.

In an embodiment of the present invention, a method is provided for determining the energy of breathing and triggering the pressure relief during expiration, the method is shown in FIG. 4; it should be noted that this method can be implemented both in hardware and in software as understood by the person skilled in the art.

At step 400 the sampling of data is started and sample points from the breathing cycle of the patient are gathered.

At step 410 the triggering point between the inspiration and expiration periods are determined.

At the next step 420 the energy content of the breathing is determined.

At step 430 the pressure curve form (e.g. amplitude, curvature, and duration) is determined from the energy analysis.

At step 440 a control signal is sent to the ventilator for controlling the pressure supplied to the user according to the determined pressure curve form.

The duration of the pressure reduction during each expiration period can be determined for instance as a function of the previous inspiration period.

In another embodiment the duration time of the pressure reduction can be determined by continuously measuring the breathing gas flow and determining the maximum flow of the expiration period and relating the duration as a function of this parameter.

In both cases the function need not be direct or linear but may be determined by a non linear algorithm. However, often it is a percentage of the determined duration parameter.

The curvature of the pressure reduction and the amplitude can be selected from pre defined curvature and amplitude configurations or determined based on input parameters (e.g. flow, pressure, current, voltage and/or other breathing parameters) using some algorithmic relationship. Pre defined configurations may be selected from an array or matrix of configurations connected to input parameters in a look up table for quick response of the overall system during use.

By measuring the energy which is presented to the patient during inhalation a system can be designed which relief's the patient during the exhalation period. Since the inhaled "energy" is always higher compared to a steady CPAP state with a fixed leakage it will be possible to calculate the inhaled energy and also the required energy drop during exhalation. The energy drop which is set as the expiratory energy drop factor can be set in percentage.

The time 303 for which the energy relief shall be active can be chosen from for example:

The exhalation trigger point 301 to the exhalation max. flow point 302 (Alt. 1 in FIG. 3).

The exhalation trigger point 301 to and the length of inspiration time 304 (time period 305 in Alt. 2 in FIG. 3).

The curve form of the pressure during the expiration phase is mostly concerned in giving a pressure relief to the user of the ventilator, i.e. a reduction of pressure from the base pressure normally supplied by the CPAP system.

It should be noted that the Figs are not to scale and used only for illustrative purposes.

It should be noted that the word "comprising" does not exclude the presence of other elements or steps than those listed and the words "a" or "an" preceding an element do not exclude the presence of a plurality of such elements. It should further be noted that any reference signs do not limit the scope of the claims, that the invention may at least in part be implemented by means of both hardware and software, and that several "means" may be represented by the same item of hardware.

The above mentioned and described embodiments are only given as examples and should not be limiting to the present invention. Other solutions, uses, objectives, and functions within the scope of the invention as claimed in the below described patent claims should be apparent for the person skilled in the art.

The invention claimed is:

1. A mechanical ventilator for treatment of breathing disorders in a patient, comprising:
a controllable pressure and breathing gas flow generator, and sensor input for receiving at least one sensor signal indicative of breathing gas pressure and/or flow,
wherein the ventilator is arranged to determine an inspiratory energy of breathing associated with the ventilator by measuring current and voltage supplied to the generator, and
wherein the ventilator is further arranged to determine an amount of pressure reduction, to be used during an expiration period, based on the inspiratory energy of breathing.

2. The ventilator according to claim 1, arranged to determine a trigger point between an inspiration and expiration phase of a breathing cycle, wherein the ventilator is controllable to reduce the pressure by the amount of pressure reduction during a period of time during the expiration phase of the breathing cycle.

3. The ventilator according to claim 2, arranged to determine the amount of pressure reduction as the inspiratory energy of breathing times an energy relief factor divided by an exhalation energy.

4. The ventilator according to claim 1, arranged to determine the inspiratory energy of breathing by measuring the pressure and flow supplied to the patient.

5. The ventilator according to claim 1, arranged to provide a continuous positive airway pressure ventilation.

6. The ventilator according to claim 1, arranged to receive further sensor signals indicative of at least one of EEG, EMG, EOG, ECG, $O_2$, $CO_2$, temperature, blood pressure, eye movements, or sound.

7. A method of increasing the comfort for a patient using a mechanical ventilator comprising a controllable pressure and breathing gas flow generator, comprising the steps of:
measuring a plurality of parameters during an inspiration phase of a breathing cycle;
determining a trigger point between the inspiration phase and a subsequent expiration phase;
determining a curve form of a pressure signal using an analysis of an inspiratory energy of breathing associated with the mechanical ventilator that is determined by measuring current and voltage supplied to the generator;
controlling the pressure of the breathing air from the mechanical ventilator, using the determined curve form of the pressure signal, during at least a portion of the subsequent expiration phase; and
controlling the mechanical ventilator to reduce the pressure during a period of time during the subsequent expiration phase of the breathing cycle, wherein an amount of pressure reduction is determined from the inspiratory energy of breathing determination.

8. The method of claim 7, wherein the trigger point between the inspiration phase and the subsequent expiration phase is determined using the mechanical ventilator.

9. The method of claim 7, wherein the amount of pressure reduction is determined as the inspiratory energy of breathing times an energy relief factor and dividing by an exhalation energy.

10. The method of claim 7, wherein the inspiratory energy of breathing is further determined by measuring the pressure and flow supplied to the patient.

11. The method of claim 7, further comprising:
providing a continuous positive airway pressure ventilation using the mechanical ventilator.

12. A mechanical ventilator system comprising:
a mechanical ventilator,
a breathing mask,
a breathing air conduit between the mechanical ventilator and the breathing mask, and
sensors for measuring data indicative of breathing condition and mechanical ventilator condition for use in a controller for controlling the supply of pressure and/or flow of breathing gas from the mechanical ventilator to a patient,
wherein the mechanical ventilator is arranged to determine an inspiratory energy of breathing associated with the mechanical ventilator by measuring current and voltage supplied to a fan in the mechanical ventilator that provides pressure and flow of breathing gas, and
wherein the mechanical ventilator is further arranged to determine an amount of pressure reduction, to be used during an expiration period, based on the inspiratory energy of breathing.

13. The system according to claim 12, wherein the mechanical ventilator is further arranged to determine a trigger point between an inspiration and expiration phase of a breathing cycle, wherein the mechanical ventilator is controllable to reduce the pressure by the amount of pressure reduction during a period of time during the expiration phase of the breathing cycle.

14. The system according to claim 13, wherein the mechanical ventilator is arranged to determine the amount of pressure reduction as the inspiratory energy of breathing times an energy relief factor divided by an exhalation energy.

15. The system according to claim 12, wherein the mechanical ventilator is further arranged to determine the inspiratory energy of breathing by measuring the pressure and flow supplied to the patient.

16. The system according to claim 12, wherein the mechanical ventilator is arranged to provide a continuous positive airway pressure ventilation.

17. The system according to claim 12, wherein the mechanical ventilator is arranged to receive sensor signals indicative of at least one of EEG, EMG, EOG, ECG, O2, CO2, temperature, blood pressure, eye movements, or sound.

\* \* \* \* \*